United States Patent [19]

Watanabe et al.

[11] Patent Number: 5,414,144
[45] Date of Patent: May 9, 1995

[54] PROPYLENE GLYCOL CYCLOHEXYL ETHER DERIVATIVES, METHOD OF PRODUCING SAME AND USES THEREOF

[75] Inventors: Tomonari Watanabe, Yamato; Izumi Yamashita, Yokohama; Masazumi Chono, Yokohama; Tetsushi Kouno, Yokohama, all of Japan

[73] Assignee: Asahi Kasei Kogyo Kabushiki Kaisha, Osaka, Japan

[21] Appl. No.: 125,094

[22] Filed: Sep. 21, 1993

[51] Int. Cl.$^6$ .................. C07C 41/00; C11D 1/722; B01F 17/42
[52] U.S. Cl. ........................... 568/670; 252/170
[58] Field of Search ............... 568/670, 662; 252/170, 252/173, 162

[56] References Cited

U.S. PATENT DOCUMENTS

| | | | |
|---|---|---|---|
| 4,308,184 | 12/1981 | Thoma et al. | 524/512 |
| 4,324,923 | 4/1982 | Kiwala et al. | 568/659 |
| 4,450,307 | 5/1984 | Moss et al. | 568/665 |
| 4,801,643 | 1/1989 | Craig | 524/832 |
| 5,225,456 | 7/1993 | Langerbeins et al. | 523/201 |

FOREIGN PATENT DOCUMENTS

| | | |
|---|---|---|
| 3-62895 | 3/1991 | Japan . |
| 3-97792 | 4/1991 | Japan . |
| 3-162496 | 7/1991 | Japan . |
| 3-227440 | 10/1991 | Japan . |
| 4-57897 | 2/1992 | Japan . |
| 4-57898 | 2/1992 | Japan . |

Primary Examiner—Arthur C. Prescott
Attorney, Agent, or Firm—Pennie & Edmonds

[57] ABSTRACT

A novel propylene glycol cyclohexyl ether derivative represented by formula I is disclosed.

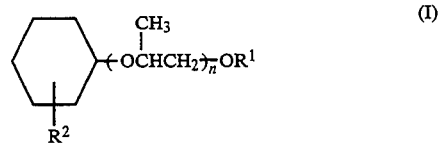

(I)

wherein $R^1$ represents a straight or branched alkyl group having 1 to 6 carbon atoms, or a cycloalkyl group having 3 to 6 carbon atoms; $R^2$ represents a hydrogen atom or a hydroxyl group; and n represents an integer of from 1 to 3.

This propylene glycol cyclohexyl ether derivative is not only extremely safe by virtue of its low toxicity and high flash point, but also has excellent detergency, low viscosity, and can impart a high film-forming ability to a resin emulsion. Further, this propylene glycol cyclohexyl ether derivative also has high hydrophobicity (and hence low water-solubility), so that it can minimize the cost and labor for disposal of waste water. Therefore, this propylene glycol cyclohexyl ether derivative is useful in various applications, for example, as a detergent, as a solvent for a wide variety of applications and as a film-forming agent.

8 Claims, 3 Drawing Sheets

PROPYLENE GLYCOL CYCLOHEXYL ETHER DERIVATIVES, METHOD OF PRODUCING SAME AND USES THEREOF

BACKGROUND OF THE INVENTION

1. Field of the Invention

The present invention relates to a propylene glycol cyclohexyl ether derivative. More particularly, the present invention is concerned with a novel propylene glycol cyclohexyl ether derivative having a cyclohexyl or monohydroxycyclohexyl group at a specific position in the molecule, and a method for producing the same. The propylene glycol cyclohexyl ether derivative of the present invention is not only extremely safe by virtue of its low toxicity and high flash point, but also has excellent detergency, low viscosity, and can impart a high film-forming ability to a resin emulsion. Further, this propylene glycol cyclohexyl ether derivative also has high hydrophobicity (and hence low water-solubility), so that it can minimize the cost and labor for disposal of waste water. Therefore, this propylene glycol cyclohexyl ether derivative is useful in various applications, for example, as a detergent, as a solvent for a wide variety of applications and as a film-forming agent. The present invention is also concerned with a detergent comprising this novel propylene glycol cyclohexyl ether derivative, which is particularly effective for removing ink used in screen printing, processing oils used in the processing of precision machinery parts and optical machinery parts, the flux used to solder electrical and electronic parts, and uncured epoxy adhesives. Furthermore, the present invention is concerned with an aqueous dispersion composition containing this novel propylene glycol cyclohexyl ether derivative, which is particularly useful as an aqueous paint.

2. Discussion of Related Art

In recent years, the prevention of environmental pollution and the improvement of work environment have been attracting great attention. Accordingly, it has become an urgent task to substitute solvents which cause environmental pollution or are toxic with solvents which do not cause these serious problems while exhibiting excellent performance.

For example, halogenated solvents, such as 1,1, 2-trichloro-1,2,2-trifluoroethane and 1,1,1-trichloroethane have low toxicity, nonflammability and excellent solvent properties and have therefore been widely used to remove processing oils used in the processing of precision machinery parts and optical machinery parts and the flux used to solder electrical and electronic parts. The use of such halogenated solvents, however, has also been found to cause serious problems, such as the destruction of the protective ozone layer surrounding the earth contributing to global warming, so that their use will be prohibited in the future.

As substitutes for the above-mentioned halogenated solvents, various solvents have been proposed. However, such substitute solvents also have posed various problems. For example, terpenes, which are non-halogenated solvents, exhibit excellent detergency, but have a disadvantageously low flash point, so that safety during use cannot be ensured.

Further, glycol monoalkyl ether derivatives have been proposed as substitute solvents (see, for example, Unexamined Japanese Patent Application Laid-Open Specification Nos. 3-162496 and 3-97792), but these conventional glycol monoalkyl ether derivatives also have problems. When the number of carbon atoms of the alkyl groups of these compounds is relatively small (as in diethylene glycol monobutyl ether), the solubility of the compounds in water is disadvantageously high, so that the waste water is likely to be contaminated with the compound, leading to difficulties in disposing the waste water. On the other hand, when the number of carbon atoms of the alkyl groups is relatively large (as in diethylene glycol monohexyl ether), the solubility of the compounds in water is low and the contamination of the waste water with the compounds can be avoided, but the compounds have disadvantageously high viscosity and thus poor detergency.

Glycol dialkyl ether derivatives have also been proposed as substitute solvents (see, for example, Unexamined Japanese Patent Application Laid-Open Specification No. 3-227400), but these compounds have drawbacks in that, for example, diethylene glycol dimethyl ether and diethylene glycol diethyl ether, which are described in the working Examples of the above Application, not only exhibit high toxicity, but also have extremely high solubility in water, so that waste water is likely to be contaminated with such compounds, leading to an increase in the cost for the disposal of the waste water.

Thus, satisfactory glycol ether type solvents, which can be safely used, for example, as detergents and paint compositions, have heretofore not been known.

Ethylene glycol solvents which were widely used in paint and ink compositions have been substituted with less toxic propylene glycol solvents, particularly propylene glycol ether derivatives, which are obtained by etherifying propylene glycol with lower alkyl groups, such as methyl, ethyl, and butyl. However, these propylene glycol ether derivatives have high solubility in water, so that the use of such derivatives causes the waste water to be contaminated therewith, leading to difficulties in disposing the waste water. Particularly, in the field of paints, there is a trend toward switching from non-aqueous paints to aqueous paints in order to reduce the amount of non-aqueous solvents used. This trend of using water as a part of the solvent has increased the above-mentioned difficulties in disposal of the waste water when water is used in combination with the propylene glycol ether derivatives.

Further, in aqueous paints, the use of film-forming agents which serve to facilitate the formation of a paint film (and which are not needed when non-aqueous solvents are employed) is needed. Examples of conventional film forming agents include, N-methylpyrrolidone (NMP), 2,2,4-trimethyl-1,3-pentanediol isobutyrate, butyl cellosolve, polypropylene glycol derivatives and the like. Such film-forming agents, however, have the problems of high hydrophilicity, unpleasant odor, toxicity and the like.

Accordingly, it has been earnestly desired to develop a novel compound having properties, such as low toxicity, excellent safety (i.e., nonflammability and a high flash point), high hydrophobicity, high detergency, high solvency, high capability to facilitate film formation, and the like, so that it can be advantageously used as a solvent, a detergent or a film-forming agent.

In order to satisfy the above-mentioned requirements, several techniques have been proposed.

For example, Unexamined Japanese Patent Application Laid-Open Specification No. 3-62895 discloses an ethylene glycol ether derivative and a propylene glycol ether derivative which have a higher alkyl group, such as an n-hexyl group. These glycol ether derivatives, however, are very poor in detergency, although their solubility in water is relatively low. When the chain lengths of the alkyl groups of such glycol ether derivatives are increased, hydrophobicity is improved, but the boiling point and viscosity become disadvantageously high. Thus, these glycol ether derivatives are not suitable for practical use.

Further, Unexamined Japanese Patent Application Laid-Open Specification Nos. 4-57897 and 4-57898 disclose the reaction of a propylene oxide with cyclohexanol. By this reaction, propylene glycol monocyclohexyl ether represented by the formula shown below is produced with a selectivity of about 100%.

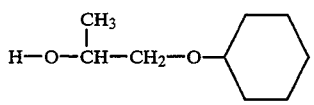

This compound, however, not only has high solubility in water, leading to difficulties in disposing waste water containing this compound, but is also disadvantageous in that it has high viscosity, poor dissolving power for oils, and low drying rate. Accordingly, this compound is not useful in practice.

Thus, there are no compounds in the art which simultaneously satisfy all of the requirements mentioned above for use as solvents, detergents and film-forming agents.

SUMMARY OF THE INVENTION

With a view toward developing a novel compound which is free from the above-mentioned drawbacks inevitably accompanying the conventional compounds, the present inventors have conducted extensive and intensive studies. As a result, it has unexpectedly been found that this goal can be attained by a novel propylene glycol cyclohexyl ether derivative in which a cyclohexyl or monohydroxycyclohexyl group is present at a specific position in the molecule.

Based on this novel finding, the present invention has been completed.

The reasons for the excellent and desired properties of the invented propylene glycol cyclohexyl ether derivative, which has a cyclohexyl or hydroxycyclohexyl group at a position opposite to the position of the cyclohexyl group in the propylene glycol cyclohexyl ether structure disclosed in the above-mentioned Unexamined Japanese Patent Application Laid-Open Specification Nos. 4-57897 and 4-57898, have not been elucidated.

In view of the knowledge that propylene glycol ether derivatives are generally poor in properties as compared to ethylene glycol ether derivatives, it is quite surprising that a propylene glycol cyclohexyl ether derivative has markedly improved properties, such as detergency, solvency and capability to facilitate film formation, simply by introducing a cyclohexyl or monohydroxycyclohexyl group at a specific position in the molecular structure of the propylene glycol. Further, considering the relationship between number of carbon atoms in a molecule and hydrophobicity, it is quite surprising that the propylene glycol cyclohexyl ether derivative of the present invention, which contains a relatively small number of carbon atoms, is extremely hydrophobic.

It is, therefore, an object of the present invention to provide a novel compound which is not only excellent in safety by virtue of its low toxicity and high flash point, but also has excellent detergency, low viscosity, high capability to facilitate film formation and high hydrophobicity (which leads to great ease in disposal of waste water), so that it is extremely useful as a detergent, a solvent for a wide variety of applications, and a film-forming agent.

Another object of the present invention is to provide a method for producing the above-mentioned novel compound.

Still another object of the present invention is to provide a detergent comprising the above-mentioned novel compound.

A further object of the present invention is to provide an aqueous dispersion composition containing the above-mentioned novel compound.

The foregoing and other objects, features and advantages of the present invention will become apparent from the following detailed description, claims and accompanying drawings.

DETAILED DESCRIPTION OF THE INVENTION

Figure 1:
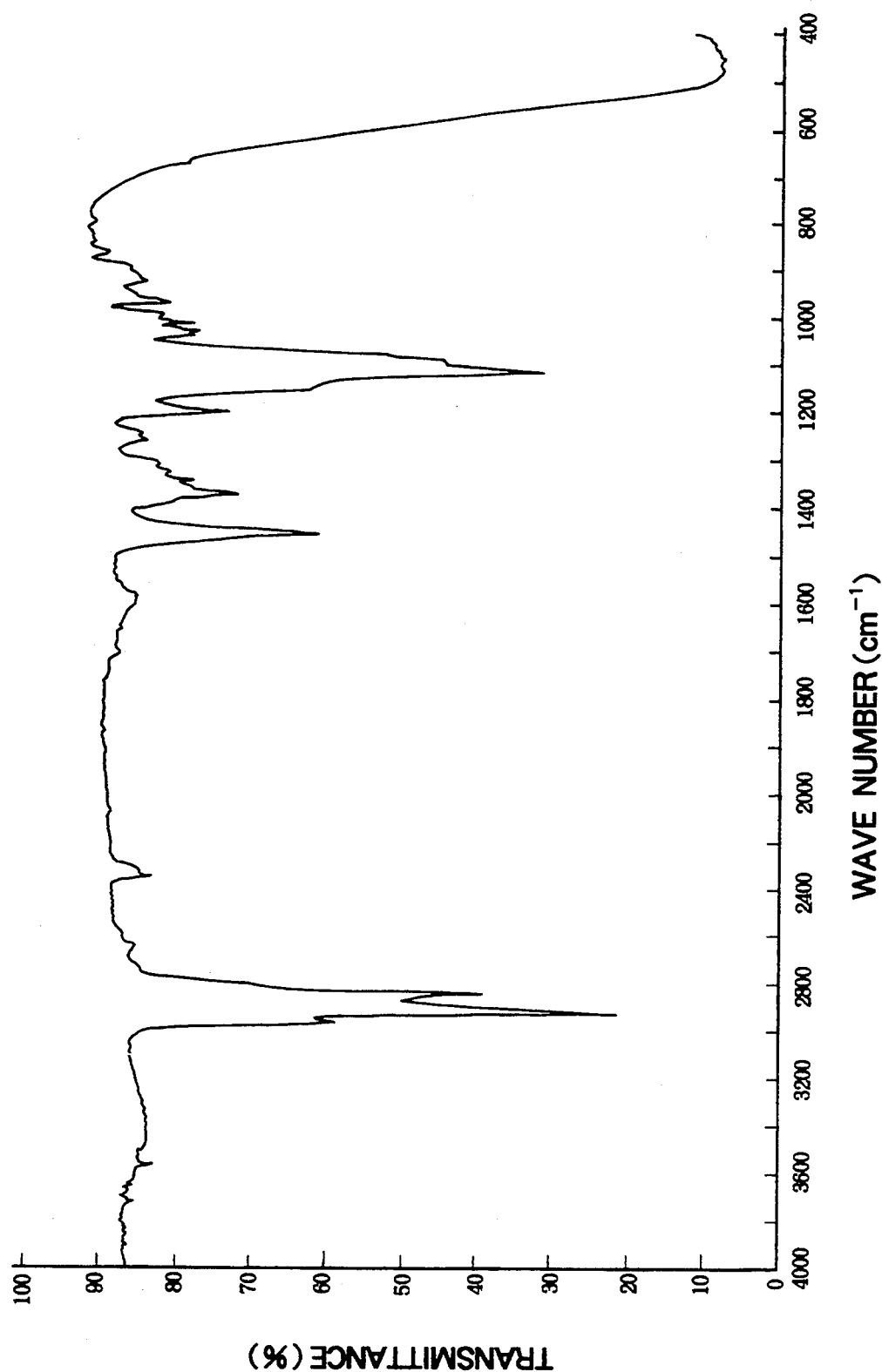
FIG. 1 is an IR spectrum of the propylene glycol cyclohexyl ether derivative of the present invention obtained in Example 1 described below.

The propylene glycol cyclohexyl ether derivative of the present invention is represented by formula I

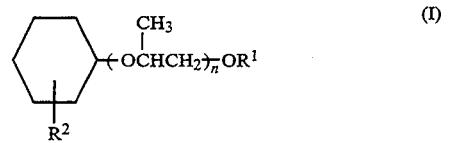

wherein $R^1$ represents a straight or branched alkyl group having 1 to 6 carbon atoms, or a cycloalkyl group having 3 to 6 carbon atoms; $R^2$ represents a hydrogen atom or a hydroxyl group; and n represents an integer of from 1 to 3.

Representative examples of $R^1$ include methyl, ethyl, isopropyl, butyl, tert-butyl, n-hexyl and cyclohexyl.

When n is 1, formula I represents a propylene glycol cyclohexyl ether derivative; when n is 2, formula Ia I represents a dipropylene glycol cyclohexyl ether derivative; and when n is 3, formula I represents a tripropylene glycol cyclohexyl ether derivative.

The propylene glycol cyclohexyl ether derivative of the invention is safe to use and has not only low toxicity but also high hydrophobicity, excellent solvency, excellent detergency and excellent capability to facilitate film formation. Therefore, the propylene glycol cyclohexyl ether derivative of the invention is extremely useful in various applications, for example, as detergents, solvents and film-forming agents.

The propylene glycol cyclohexyl ether derivative of the present invention can be easily produced with high selectivity.

Accordingly, in another aspect of the present invention, there is provided a method for producing a propylene glycol cyclohexyl ether derivative represented by formula I shown below,

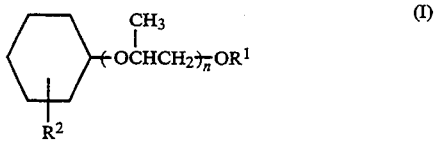

wherein $R^1$ represents a straight or branched alkyl group having 1 to 6 carbon atoms, or a cycloalkyl group having 3 to 6 carbon atoms; $R^2$ represents a hydrogen atom or a hydroxyl group; and n represents an integer of from 1 to 3,
which comprises reacting a propylene glycol ether represented by formula II shown below,

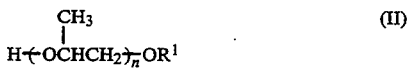

wherein $R^1$ represents a straight or branched alkyl group having 1 to 6 carbon atoms, or a cycloalkyl group having 3 to 6 carbon atoms; and n represents an integer of from 1 to 3,
with cyclohexene, cyclohexanol or cyclohexene oxide in the presence of a catalyst.

Representative examples of propylene glycol ethers represented by formula II include 1-methoxy-2-propanol, 1-ethoxy-2-propanol, 1-isopropoxy-2-propanol, 1-butoxy-2-propanol, 1-tert-butoxy-2-propanol, 1-hexyl-2-propanol, and the like.

For example, propylene glycol methyl cyclohexyl ether according to the present invention can be produced by heating propylene glycol methyl ether and cyclohexene in an autoclave in the presence of an acid catalyst, and then separating the desired product from the reaction mixture.

As mentioned above, Unexamined Japanese Patent Application Laid-Open Specification Nos. 4-57897 and 4-57898 disclose the reaction of propylene oxide with cyclohexanol by heating in the presence of an acid or an alkali. It is well known in the art that use of this method results in propylene glycol cyclohexyl ether represented by formula III:

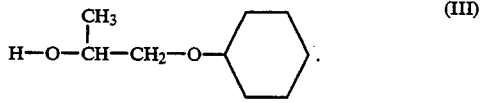

Propylene glycol cyclohexyl ether of formula III is different in structure from propylene glycol cyclohexyl ether derivative I of the present invention. That is, one difference involves the position of the cyclohexyl group of structure I, which is opposite to the position of the cyclohexyl group in structure III. Another difference involves the fact that compound III has a free terminal hydroxyl group, whereas compound I of the present invention has both terminal hydroxyl groups converted to ether groups. In addition, the free terminal hydroxyl group of compound III cannot be converted to an ether group even by reaction with an aliphatic alcohol.

For use of the method of the present invention, any conventional reaction solvent may be employed as long as it does not adversely affect the reaction. Examples of reaction solvents include halogenated hydrocarbons; aromatic hydrocarbons, such as benzene, toluene and xylene; aliphatic hydrocarbons, such as hexane, decane and cyclohexane; amides, such as dimethylformamide (DMF), dimethylacetamide (DMAc) and N-methylpyrrolidone; and water. These solvents may be used individually or in combination.

The molar ratio of propylene glycol ether represented by formula II to cyclohexene, cyclohexanol or cyclohexene oxide is selected in the range from 20/1 to 1/20.

The reaction temperature may be varied depending upon other reaction conditions, such as the types of the starting materials and solvent, but it is generally in the range from 50° C. to 200° C.

The reaction time is generally in the range from 30 minutes to 20 hours.

The reaction pressure may be varied depending upon the reaction temperature, but it is generally in the range from atmospheric pressure to 10 kg/cm².

The catalyst is usually selected from customary acids. Examples of such acids include: solid acids, such as zeolite and mordenite; acidic resins, such as a fluorosulfonic acid resin; inorganic acids, such as sulfuric acid; organic acids, such as trifluoromethanesulfonic acid and benzenesulfonic acid; and the like. These catalysts may be used individually or in combination. On the other hand, when cyclohexene oxide is used as the reactant, the catalyst can be an alkali catalyst, such as sodium hydroxide, potassium hydroxide or basic ion exchange resin. The amount of the catalyst is generally 0.001 to 50% by weight, based on the total weight of the starting material and the reactant.

The type of the reactor is not particularly limited. Customary reactors can be employed, such as an autoclave or a tube-type reactor.

The propylene glycol cyclohexyl ether derivative of the present invention can be identified by NMR, IR spectroscopy, gas chromatography (GC) and mass spectrometry.

In still another aspect of the present invention, there is provided a detergent comprising at least one propylene glycol cyclohexyl ether derivative of the present invention represented by formula I.

Representative examples of propylene glycol cyclohexyl ether derivatives represented by formula I to be used in the detergent of the present invention include monopropylene glycol cyclohexyl ether derivatives, such as propylene glycol methyl cyclohexyl ether (PGMCHE), propylene glycol ethyl cyclohexyl ether (PGECHE), propylene glycol propyl cyclohexyl ether (PGPCHE), propylene glycol isopropyl cyclohexyl ether (PGiPCHE), propylene glycol n-butyl cyclohexyl ether (PGBCHE), propylene glycol isobutyl cyclohexyl ether (PGiBCHE), propylene glycol tert-butyl cyclohexyl ether (PGtBCHE), propylene glycol n-pentyl cyclohexyl ether (PGPECHE), propylene glycol cyclopentyl cyclohexyl ether (PGCPCHE), propylene glycol n-hexyl cyclohexyl ether (PGHCHE), propylene glycol methyl cyclopentyl cyclohexyl ether (PGMCPCHE), propylene glycol dicyclohexyl ether (PGDCHE) and propylene glycol methyl monohydroxycyclohexyl ethers (PGMHCHE), such as 2-hydroxycyclohexyloxymethoxypropane (i.e., propylene glycol methyl 2-hydroxycyclohexyl ether); and dipropylene glycol cyclohexyl ether derivatives and tripropylene glycol cyclohexyl ether derivatives, each having one or more ether moieties corresponding to those of the above-mentioned monopropylene glycol ether derivatives. Preferred examples are PGMCHE, PGECHE, PGiPCHE, PGtBCHE, PGMHCHE, PGMHCHE and dipropylene glycol methyl cyclohexyl ether (DPGMCHE). Especially preferred are PGMCHE, PGMHCHE and DPGMCHE, i.e., propylene glycol methyl cyclohexyl ether, propylene glycol methyl monohydroxycyclohexyl ether and dipropylene glycol methyl cyclohexyl ether. These propylene glycol cyclohexyl ether derivatives may be used individually or in combination.

The detergent of the present invention may optionally include additives, such as aliphatic hydrocarbons, alicyclic hydrocarbons, ketones, esters, alkanolamines, nonionic surface active agents, rust-preventive agents, water, and the like, to thereby form a detergent composition. These additives may be used individually or in combination. When these additives are employed, it is preferred to select those which do not lower the flash point of the detergent composition.

Examples of aliphatic hydrocarbons include decane, undecane, dodecane, tridecane, tetradecane, pentadecane, 2,2,4,4,6,8,8-heptamethylnonane, 2,6,10,14-tetramethyl pentadecane, and the like. Examples of alicyclic hydrocarbons include menthane, bicyclohexyl, cyclododecane, decalin, and the like. These hydrocarbons may be used individually or in combination. The amount of the hydrocarbon is generally 0–90% by weight, preferably 0–70% by weight, based on the total weight of the detergent composition.

Examples of ketones include various isomers of pentanone, hexanone, heptanone and octanone, phorone, isophorone, cyclohexanone, methylcyclohexanone, acetophenone, and the like. These ketones may be used individually or in combination. The amount of the ketone is generally 0–90% by weight, preferably 0–70% by weight, based on the total weight of the detergent composition.

Examples of esters include the alkyl or cycloalkyl esters of acetic, propionic, butyric, isobutyric, isovaleric, oxalic, malonic, glutaric, succinic, adipic acids; the acetic acid ester of glycol ether; γ-butyrolactone; and the like. These esters may be used individually or in combination. The amount of the ester is generally 0–90% by weight, preferably 0–70% by weight, based on the total weight of the detergent composition.

Examples of alkanolamines include monoethanolamine, diethanolamine, triethanolamine, N-methylethanolamine, N-ethylethanolamine, N-propylethanolamine, and the like. These alkanolamines may be used individually or in combination. The amount of the alkanolamine is generally 0–30% by weight, preferably 0–15% by weight, based on the total weight of the detergent composition.

Examples of nonionic surface active agents include a polyoxyethylene alkyl ether, a polyoxyethylene alkyl phenyl ether, a polyoxyethylene polystyryl phenyl ether, polyoxyethylene-polyoxypropylene glycol, a polyoxyethylene-polyoxypropylene alkyl ether, a partial ester of a polyoxyethylene-glycerine polyhydric alcohol with a fatty acid, partial esters of other polyhydric alcohols with fatty acids, a fatty acid ester of polyoxyethylene, a fatty acid ester of polyglycerin, a fatty acid diethanolamide, a polyoxyethylene alkylamine, a partial ester of triethanolamine with a fatty acid, and the like. These nonionic surface active agents may be used individually or in combination. The amount of the surface active agent is generally 0–30% by weight, preferably 0–15% by weight, based on the total weight of the detergent composition.

Examples of rust-preventive agents include fatty acids, metallic soaps, amines, esters, dicyclohexylammonium nitrite, diisopropylamine nitrite, dicyclohexylamine caprate, benzotriazole, and the like. These rust-preventive agents may be used individually or in combination. The amount of the rust-preventive agent is generally 0–0.1% by weight, based on the total weight of the detergent composition.

The detergent of the present invention can be used for cleaning purposes in various fields. For example, the detergent of the present invention is effective for removing ink used in screen printing; for removing processing oils, such as a cutting oil used for processing precision machinery parts and optical machinery parts, a pressing oil, a drawing oil, a heat-treatment oil, a rust-preventive oil, wax, a lubricating oil and grease; for removing a flux used for soldering electrical and electronic parts; and for removing an uncured epoxy adhesive. The detergent of the present invention has excellent detergency, low solubility in water, high flash point and less toxicity, thus solving the problems of the conventional detergents.

In a further aspect of the present invention, there is provided an aqueous dispersion composition comprising:

(a) a continuous phase of an aqueous dispersion medium;

(b) a dispersed phase dispersed in the continuous phase (a); and (c) 0.5–30% by weight, based on the weight of the dispersed phase (b), of at least one propylene glycol cyclohexyl ether derivative represented by formula I.

Examples of the component described in (a) above, i.e., a continuous phase of an aqueous dispersion medium, include water, and mixtures of water with straight chain or branched alcohols, each having 1 to 10 carbon atoms, or water-miscible ether derivatives, such as dioxane.

Examples of the component described in (b) above, i.e., a dispersed phase dispersed in the continuous phase described in (a) above, include a polyurethane, a polyacrylate, a styrene-butadiene copolymer, polyvinyl acetate, polyvinylidene chloride, a fluoro polymer, and the like. Preferred examples are a polyurethane and a polyacrylate.

The aqueous dispersion composition of the present invention is characterized by advantageously low minimum film-forming temperature and viscosity. Further, because of the very high hydrophobicity of the component described in (c) above, the aqueous dispersion composition of the present invention can minimize the cost for disposal of waste water.

Representative examples of propylene glycol cyclohexyl ether derivatives represented by formula I as the component described in (c) above of the aqueous dispersion composition include propylene glycol methyl cyclohexyl ether, propylene glycol tert-butyl cyclohexyl ether, propylene glycol methyl monohydroxycyclohexyl ether, dipropylene glycol methyl cyclohexyl ether, tripropylene glycol methyl cyclohexyl ether, and the like. Preferred examples are propylene glycol methyl cyclohexyl ether, propylene glycol methyl monohydroxycyclohexyl ether or dipropylene glycol methyl cyclohexyl ether.

The amount of the component described in (c) above may be varied depending upon the amount or the type of the solvent, and the type of the component described in (b) above, i.e., the dispersed phase, however, it is generally 0.5–30% by weight, based on the weight of the dispersed phase described in (b) above. When the amount of the component in described (c) above is less than 0.5% by weight, a satisfactory capability to facilitate film formation is not attained. On the other hand, if the amount exceeds 30% by weight, the film formation rate becomes disadvantageously low.

There is no particular limitation with respect to the manner in which the aqueous dispersion composition of the present invention is prepared from components described in (a), (b) and (c) above. Components described in (a), (b) and (c) above may be mixed together at the same time. Alternatively, the component described in (c) above, i.e., at least one propylene glycol cyclohexyl ether derivative represented by formula I, may be added to an aqueous dispersion comprised of components described in (a) and (b) above. Component of (c) above may also be added to a commercially available aqueous dispersion comprised of components of (a) and (b) above.

When the dispersed phase described in (b) above consists essentially of a polyurethane or a polyacrylate, the aqueous dispersion composed of such a dispersed phase and an aqueous dispersion medium is hereinafter frequently referred to as "polyurethane emulsion" or "polyacrylate emulsion" for the sake of convenience.

There is no particular limitation with respect to the polyurethane emulsion to be used in the present invention, and any polyurethane emulsion of anionic, cationic, or nonionic type may be used.

The polyurethane emulsion can be produced by various methods (see, for example, Unexamined Japanese Patent Application Laid-Open Specification No. 49-128997).

For example, the following method is useful. An organic polyisocyanate, a compound containing at least two active hydrogen atoms reactive with an isocyanate and having a number average molecular weight of 300–50000, and a short chain diol having a carboxylic acid group or a carboxylic acid salt group are reacted to thereby obtain a urethane prepolymer having a terminal isocyanate group. In the reaction, organic solvents inert to the isocyanate are used. Examples of solvents include acetone, methyl ethyl ketone, toluene, dioxane, N,N-dimethylformamide, N-methylpyrrolidone, tetrahydrofuran, and the like.

The above-mentioned compound containing at least two active hydrogen atoms can be selected from compounds having a terminal hydroxyl, carboxyl, amino or mercapto group, or the like. Examples of active hydrogen-containing compounds include a polycarbonate diol, a polyester diol, a polyether diol, a polycaprolactone diol, a polyamide diol, a polythioether diol, and the like.

Examples of polycarbonate diols include those obtained by reacting at least one glycol selected from the group consisting of ethylene glycol, propylene glycol, 1,3-propanediol, 1,4-butanediol, 1,5-pentanediol, 3-methyl-1,5-pentanediol, 1,9-nonanediol, 1,8-nonanediol, neopentylglycol, diethylene glycol, dipropylene glycol, 1,4-cyclohexanediol, 1,4-cyclohexanedimethanol, bisphenol-A and hydrogenated bisphenol-A, with dimethyl carbonate, diphenyl carbonate, ethylene carbonate, phosgene, or the like.

Examples of polyester diols include those obtained by reacting the above-mentioned glycol with succinic acid, adipic acid, azelaic acid, sebacic acid, dodecanedicarboxylic acid, maleic anhydride, fumaric acid, 1,3-cyclopentanedicarboxylic acid, 1,4-cyclohexanedicarboxylic acid, terephthalic acid, isophthalic acid, phthalic acid, naphthalenedicarboxylic acid, or the like.

Examples of polyether diols include those obtained by the conventional addition polymerization of at least one monomer selected from the group consisting of ethylene oxide, propylene oxide, butylene oxide, styrene oxide, epichlorohydrin, tetrahydrofuran and cyclohexene oxide, by using as an initiator at least one compound having at least two active hydrogen atoms, such as ethylene glycol, diethylene glycol, triethylene glycol, propylene glycol, trimethylene glycol, 1,3-butanediol, 1,4-butanediol, 1,6-hexanediol, neopentyl glycol, glycerin, trimethylolethane, trimethylolpropane, sorbitol, sucrose, aconitic sugar, trimellitic acid, hemimellitic acid, phosphoric acid, ethylenediamine, diethylenetriamine, triisopropanolamine, pyrogallol, dihydroxybenzoic acid, hydroxyphthalic acid, 1,2,3-propanetrithiol, and the like.

Examples of short chain diols having a carboxylic acid group or a salt thereof include 2,2-dimethylolpropionic acid, 2,2-dimethylolbutyric acid, 2,2-dimethylolvaleric acid, and salts thereof.

Examples of organic polyisocyanates include aromatic diisocyanates, such as tolylene diisocyanate (TDI) (i.e., 2,4-tolylene diisocyanate, 2,6-tolylene diisocyanate or a mixture thereof), diphenylmethane-4,4-diisocyanate (MDI), naphthalene-1,5-diisocyanate (NDI), 3,3-dimethyl-4,4-biphenylene diisocyanate (TODI), crude TDI (i.e., a mixture of TDI and an oligomer thereof), polymethylenepolyphenyl polyisocyanate, crude MDI (i.e., a mixture of MDI and an oligomer thereof), xylylene diisocyanate (XDI) and phenylene diisocyanate; and aliphatic diisocyanates, such as 4,4-methylenebisdicyclohexyl diisocyanate (hydrogenated MDI), hexamethylene diisocyanate (HDI), isophorone diisocyanate (IPDI) and cyclohexylene diisocyanate (hydrogenated XDI).

If desired, the prepolymer obtained by the above-mentioned reaction may be neutralized. Then, the prepolymer is dispersed in water to obtain a urethane prepolymer emulsion. If desired for facilitating emulsification, a surface active agent may be employed. The emulsified prepolymer is then subjected to polymerization by the use of a chain extender followed by the removal of the solvent, thereby obtaining a polyurethane emulsion.

Examples of chain extenders include short chain diols, such as ethylene glycol and 1,4-butanediol; diamines, such as ethylenediamine, propylenediamine, hexamethylenediamine, tolylenediamine, xylylenediamine, diphenyldiamine, diaminodiphenylmethane, diaminocyclohexylmethane, piperazine, 2-methylpiperazine and isophoronediamine; water; and the like.

Examples of neutralizing agents include amines, such as trimethylamine, triethylamine, tri-n-propylamine, tributylamine and triethanolamine; sodium hydroxide; pottasium hydroxide; ammonia; and the like.

Examples of surface active agents include anionic surface active agents, such as sodium dodecylbenzenesulfonate, sodium dodecylsulfate and an alkyl aryl polyether sulfate; nonionic surface active agents, such as a polyoxyethylene alkyl ether and a polyoxyethylene alkyl aryl ether; and protective colloids, such as polyvinyl alcohol and polyacrylic acid; and the like.

The respective amounts of the organic polyisocyanate, the active hydrogen-containing compound, the short chain diol having a carboxylic acid group or a carboxylic acid salt group, the chain extender, the neutralizing agent and the surface active agent to be used in the production of the polyurethane emulsion may be varied depending upon the molecular weight of the polyurethane as the dispersed phase described in (b) above, the amount of the soft segment of the polyurethane, and the like.

There is no limitation with respect to the amount of water to be used for dispersing the prepolymer therein, but the preferred amount is such that, after dispersing the prepolymer in water, the solids content of the aqueous dispersion becomes 10–60% by weight.

As a method for dispersing the prepolymer in water, a method in which a predetermined amount of water is added dropwise to the prepolymer while stirring the prepolymer, may be employed. A method in which the prepolymer is dropwise added to a predetermined amount of water while vigorously stirring the water may also be employed.

As mentioned above, the urethane prepolymer emulsion obtained by dispersing the prepolymer in water is subjected to polymerization by the use of a chain extender followed by the removal of the solvent, thereby obtaining a polyurethane emulsion.

The obtained aqueous polyurethane dispersion, i.e., polyurethane emulsion, is subjected to distillation to remove the solvent contained therein by, for example, using the following procedure. In place of the use of a customary anti-foaming agent, a predetermined amount of component described in (c) above, i.e., the propylene glycol cyclohexyl ether derivative represented by formula I, is added to the aqueous dispersion, which is then subjected to distillation to remove the solvent. By using this procedure, the use of an anti-foaming agent can be omitted by virtue of the excellent anti-foaming activity of the component described in (c) above. For this procedure, to increase the anti-foaming effect of the component of (c) above, the component may be added in an excess amount of up to about 40% by weight, based on the weight of the dispersed (polyurethane) phase of (b) above. In such a case, after the removal of the solvent, the distillation is continued until the amount of the component from (c) has become 0.5–30% by weight, based on the weight of the dispersed (polyurethane) phase of (b) above.

The aqueous polyurethane dispersion composition of the present invention obtained as described above forms excellent films, and can advantageously be employed in various fields, such as in the fields of coatings and adhesives. Further, since this aqueous polyurethane dispersion composition does not require the addition of hydrophylic additives, such as N-methylpyrrolidone (NMP), as film-forming agents, the cost of waste water disposal can be reduced to a minimum.

There is no limitation with respect to the polyacrylate emulsion to be used in the present invention and any of those customarily used may be employed. Examples of polyacrylate emulsions include a crosslinked type polyacrylate emulsion and a core-shell type polyacrylate emulsion in which the core is crosslinked and surrounded by an uncrosslinked shell. These polyacrylate emulsions may be used individually or in combination.

The polyacrylate emulsion to be used in the present invention can be produced by customary emulsion polymerization methods (see, for example, Examined Japanese Patent Application Publication Specification No. 55-9432).

For example, the starting acrylic monomer composition comprises at least one member selected from (1) an $\alpha,\beta$-ethylenically unsaturated carboxylic acid, (2) a hydroxyalkyl-containing ester of an $\alpha,\beta$-ethylenically unsaturated carboxylic acid and (3) an alkyl ester of an $\alpha,\beta$-ethylenically unsaturated carboxylic acid, and optionally (4) other copolymerizable monomers.

Examples of $\alpha,\beta$-ethylenically unsaturated carboxylic acids described in group (1) above include acrylic, $\alpha$-chloroacrylic, methacrylic, itaconic, maleic, fumaric, crotonic, citraconic, or mesaconic acid, and mixtures thereof.

Examples of hydroxyalkyl-containing esters of $\alpha,\beta$-ethylenically unsaturated carboxylic acids described in group (2) above include 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 4-hydroxybutyl acrylate, 4-hydroxybutyl methacrylate, diethylene glycol monoacrylate, diethylene glycol monomethacrylate, and the like.

Examples of alkyl esters of $\alpha,\beta$-ethylenically unsaturated carboxylic acids described in group (3) above include methyl acrylate, methyl methacrylate, ethyl acrylate, ethyl methacrylate, n-propyl acrylate, n-propyl methacrylate, isopropyl acrylate, isopropyl methacrylate, butyl acrylate, butyl methacrylate, lauryl acrylate, lauryl methacrylate, stearyl acrylate, stearyl methacrylate, hexyl acrylate, 2-ethylhexyl methacrylate, heptyl acrylate and heptyl methacrylate, and other similar esters having 25 or less carbon atoms in their alkyl moiety.

Examples of other copolymerizable monomers described in group (4) above include polyfunctional monomers, such as 1,4-butylene glycol diacrylate, 1,6-hexane glycol diacrylate, pentaerythritol triacrylate, trimethylolpropane triacrylate, triethylene glycol dimethacrylate, tetraethylene glycol dimethacrylate, 1,3-butylene glycol dimethacrylate, 1,4-butylene glycol dimethacrylate, propylene glycol dimethacrylate, trimethylol propane trimethacrylate, divinylbenzene and trivinylbenzene; styrene; $\alpha$-alkylstyrene; $\alpha$-chlorostyrene; vinyltoluene; acrylonitrile; vinyl acetate, and the like. When a polyfunctional monomer is used, a film having high hardness can be formed.

The emulsifying agent and the polymerization initiator to be used for the production of the polyacrylate emulsion are not particularly restricted, and may be selected depending upon the type of the monomer composition used so that the polymerization reaction can proceed efficiently.

Examples of emulsifying agents include anionic surface active agents, such as a sulfonic acid ester of a higher alcohol, alkylbenzene sulfonate, polyoxyethylene alkyl sulfate and benzene sulfonate; and nonionic surface active agents, such as polyoxyethylene alkyl ether, polyoxyethylene alkyl phenol ether, an ethylene oxide-propylene oxide block polymer and a sorbitan derivative.

Examples of polymerization initiators include persulfates, such as potassium persulfate and ammonium persulfate; peroxides, such as hydrogen peroxide, benzoyl peroxide and cumene hydroperoxide; azobisisobutyronitrile; and the like.

The aqueous polyacrylate dispersion composition of the present invention can form an excellent protective film on various types of substrates, such as wood, concrete and a paint film. The protective film formed from this aqueous polyacrylate dispersion composition not only has excellent transparency and luster but is also excellent in stain resistance, durability and abrasion resistance. Further, this film is very flexible, so that the film can follow the bending of the substrate on which it is formed.

Further, the aqueous polyacrylate dispersion composition of the present invention can advantageously be used to produce a paint or an enamel. A paint or an enamel can be readily produced by adding thereto customary additives. Examples of such additives include pigments; loading pigments, such as calcium carbonate, talc, clay, mica powder and baryte; a potassium, sodium, or ammonium salt of polyphosphoric acids, such as hexametaphosphoric acid; customary anionic or nonionic surface active agents; and dispersing and thickening agents, such as methyl cellulose, ethyl cellulose, propyl cellulose, carboxymethyl cellulose and polyvinyl alcohol.

The propylene glycol cyclohexyl ether derivative of the present invention not only has low toxicity and high safety, but is also excellent in hydrophobicity, detergency, solvency and capability to facilitate film formation, so that it can advantageously be used in various fields as a detergent, a solvent, a coating, and a paint without the danger of causing problems on health and environment while minimizing the cost of waste water disposal.

PREFERRED EMBODIMENT OF THE INVENTION

Hereinbelow, the present invention will be illustrated with reference to the following Examples and Comparative Examples, which, however, should not be construed as limiting the present invention.

In the Examples and Comparative Examples, various measurements were done as follows.

(1) IR Absorption Spectroscopy

The IR absorption spectroscopy was conducted using apparatus FT/IR-5300 (manufactured by JASCO, Japan).

(2) Gas Chromatography (GC)

The GC was conducted using apparatus GC-8A (G-column, 20 m) (manufactured by Shimadzu Corporation, Japan).

(3) Solubility ("water in" and "in water")

10 g of a sample compound (liquid) was mixed with 10 g of water and then allowed to stand still for 30 minutes, so that the mixture was permitted to separate into a sample compound layer and an aqueous layer. Then, the water content of the sample compound layer was measured using a Karl Fischer moisture meter manufactured by Kyoto Electronics Co., Ltd., Japan, and the obtained value was taken as a solubility of water in the sample compound. The content of the sample compound in the aqueous layer was measured using GC and the obtained value was taken as a solubility of the sample compound in water.

(4) Boiling Point

The boiling point was determined from the temperature and pressure of the vapor at the top of the distillation column.

(5) Flash Point

The flash point was measured in accordance with JIS-K2265.

(6) Separability from Water

An equivolume mixture of a sample compound and water was vigorously shaken and then allowed to stand. After a period of 5 minutes, the degree of separation of the sample compound from water was judged by the naked eye.

Results were evaluated as "separated well" or "not separated".

(7) Degreasing Rate

A 30-mesh stainless steel net (having a size of 2 cm × 5 cm) was immersed in a press oil (Uni Press DP-120, manufactured by Nippon Sekiyu Kagaku Co., Ltd., Japan) so that about 0.5 g of the press oil was adhered to the net. Then, the press oil-carrying net was subjected to ultrasonic cleaning in 100 ml of a sample compound, at 40° C. for 1 minute. The residual oil on the net was removed with carbon tetrachloride, and the amount of the residual oil was measured by means of an oil content meter, thereby determining a degreasing rate. Results were evaluated as "99% or more", "90% to less than 99%", or "less than 90%".

(8) Rosin Dissolution Rate

About 0.5 g of rosin was melted and then shaped into a tablet. Then, the rosin tablet was immersed in 50 ml of a sample compound for 7 minutes while shaking. Then, the dry weight of the rosin tablet was measured, thereby determining a reduction in the weight of the rosin. Results are evaluated as "30% or more", "15% to less than 30%", or "less than 15%".

(9) Viscosity

The viscosity was measured at 25° C. using a digital viscometer (Model DVL-B, manufactured by Toki Sangyo Co., Ltd., Japan).

(10) Relative Drying Rate 10 g of a sample compound and 10 g of a glycol ether-type detergent (Elease M-9000, manufactured by Asahi Kasei Kogyo K.K., Japan) were individually placed in an oven and heated at 50° C. for 20 minutes. Then, a measurement was done with respect to the decrease in the weight of the sample compound as well as the decrease in the weight of Elease M-9000. The relative drying rate was calculated according to the following formula:

$$\text{Relative drying rate (\%)} = \frac{\text{Decrease in the weight of sample compound (g)}}{\text{Decrease in the weight of Elease M-9000 (g)}} \times 100$$

(11) Oil Solubility Characteristics

Each of the oils mentioned below was individually added to 100 g of a sample compound while stirring until a saturation of the sample compound with the oil was reached. The solubility (%) was expressed in terms of the percent expression of the weight of the oil dissolved in 100 g of the sample compound, with the dissolution of 100 g of the oil being taken as 100%. For example, when the amount of the oil dissolved was n g, the solubility was expressed as n %. The above-mentioned oils were: a mineral oil (Smoil PS-260, manufactured by Matsumura Sekiyu Kenkyusho, Japan), a drawing oil (Daphne Masterdraw 533WD, manufactured by Idemitsu Kosan Co., Ltd., Japan), a press oil (Uni Press DP-120, manufactured by Nippon Sekiyu Co., Ltd., Japan) and a rosin oil (sold by Kishida Kagaku Co., Ltd., Japan).

Results were evaluated according to the following classification:
A: 50% or more
B: 20% to less than 50%
C: 10% to less than 20%
D: 2% to less than 10%
E: Less than 2%

EXAMPLE 1

27 g (0.3 mole) of propyrene glycol methyl ether (hereinafter referred to as "PM"), 50 g (0.6 mole) of cyclohexene and 5 g of Nafion ® (tradename of a fluorinated sulfonic acid resin manufactured by E.I. Du Pont De NEMOURS AND COMPANY, U.S.A.) were placed in a 100 ml glass autoclave (manufactured by Taiatsu Garasu Co., Ltd., Japan) and a reaction was allowed to proceed at 120° C. for 6 hours. The reaction pressure was 1.8 kg/cm$^2$. Results of the analysis of the resultant reaction mixture by GC showed that the conversion of PM was 28% and the selectivity for propyrene glycol methyl cyclohexyl ether (hereinafter referred to as "PGMCHE") was 99%, and that by-products, such as dipropyrene glycol, were not formed. The obtained reaction mixture was dried on sodium sulfate and then, subjected to distillation, to thereby obtain 14 g of PGMCHE as a desired product. The IR spectrum of the product is shown in FIG. 1.

Other properties [a boiling point, a flash point, solubility (in water), solubility (water in), separability from water, detergency, viscosity, relative drying rate and oil solubility characteristics] of the product were measured and results are shown in Tables 1 and 2.

EXAMPLE 2

Figure 2:
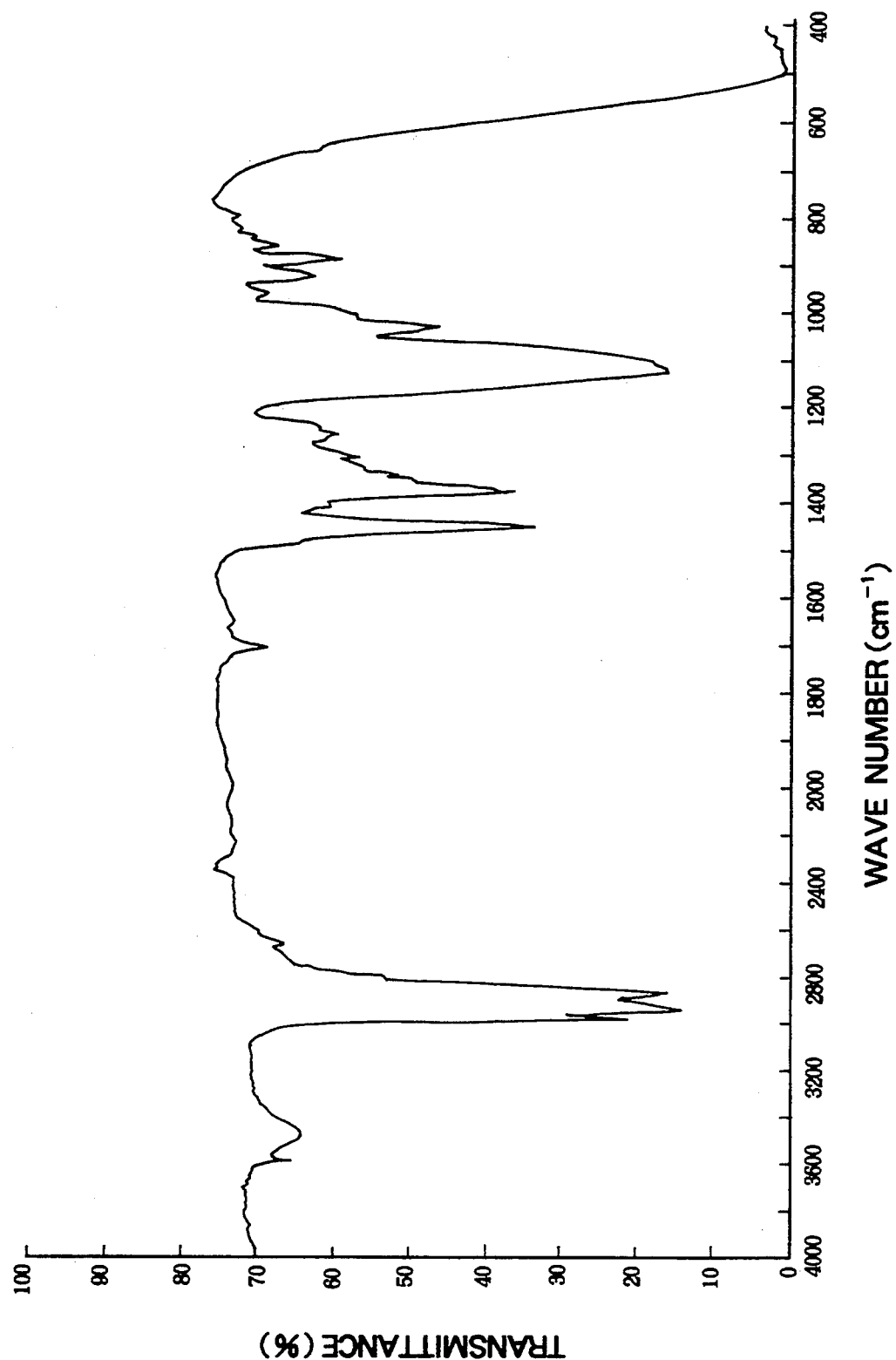
FIG. 2 is an IR spectrum of the propylene glycol cyclohexyl ether derivative of the present invention obtained in Example 2 described below.

Substantially the same procedure as in Example 1 was repeated except that 30 g of propyrene glycol ethyl ether (PE) was used instead of PM, to thereby obtain 10 g of propyrene glycol ethyl cyclohexyl ether (hereinafter referred to as "PGECHE") as a desired product. The IR spectrum of the product is shown in FIG. 2. Other properties of the product were measured and results are shown in Table 1.

EXAMPLE 3

Figure 3:
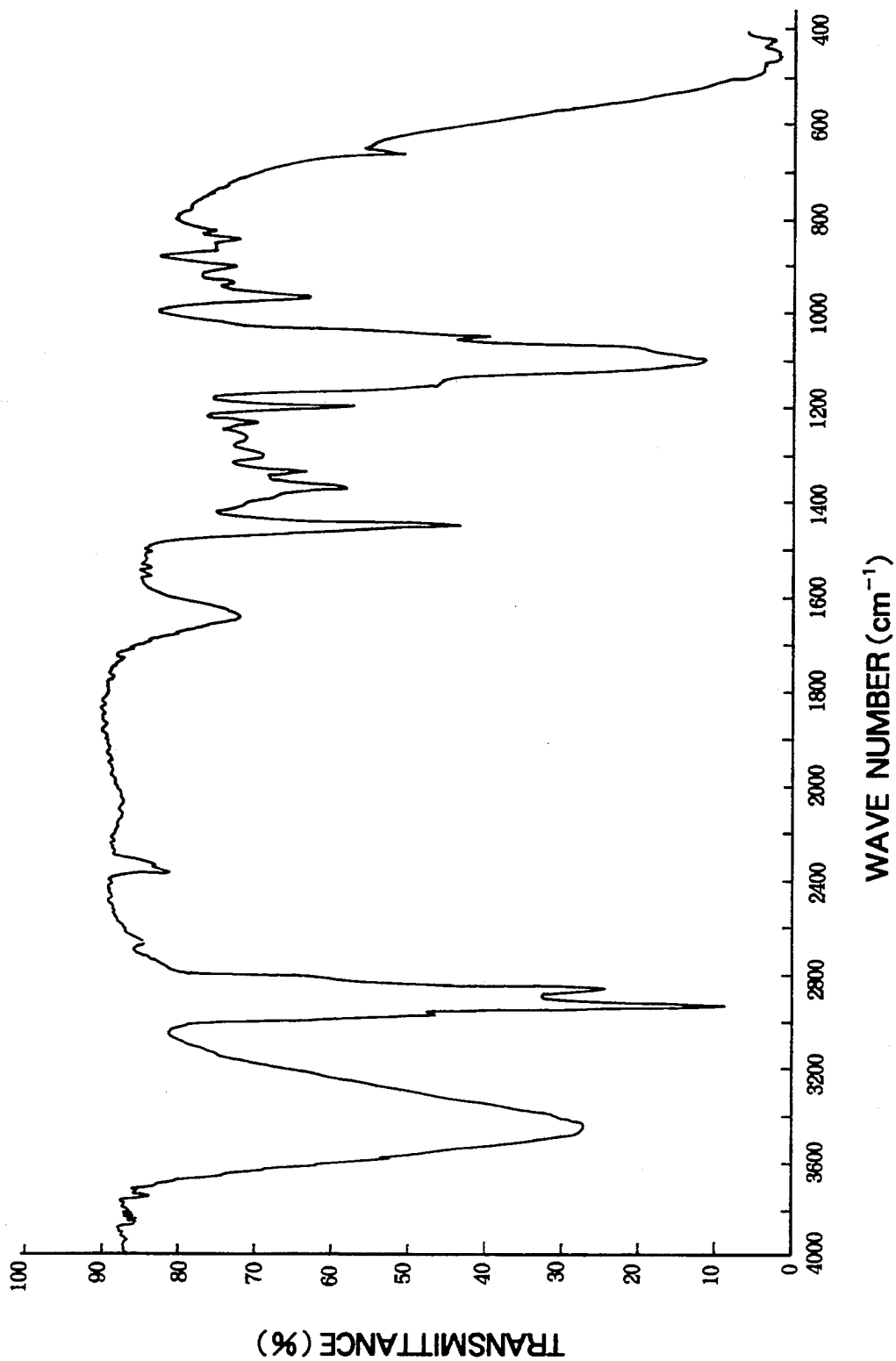
FIG. 3 is an IR spectrum of the propylene glycol cyclohexyl ether derivative of the present invention obtained in Example 3 described below.

45 g (0.5 mole) of propylene glycol methyl ether (PM), 33 g (0.33 mole) of cyclohexene oxide and 0.3 g (0.007 mole) of sodium hydroxide were charged in a 100 ml eggplant type flask equipped with a reflux tube, and a reaction was allowed to proceed under reflux at a temperature for a reflux reaction for 10 hours. Results of the analysis of the resultant reaction mixture by GC showed that the conversion of PM was 20%. Then, the obtained reaction mixture was subjected to distillation, to thereby obtain 17 g of 2-hydroxycyclohexyloxymethoxypropane, i.e., propylene glycol methyl 2-hydroxycyclohexyl ether (hereinafter referred to as "PGMHCHE"). The IR spectrum of the product is shown in FIG. 3. Other properties of the product were measured and results are shown in Table 1.

COMPARATIVE EXAMPLES 1 TO 8

Properties of the below-mentioned commercially available glycol ether products were measured and results of the measurements are shown in Table 1.

COMPARATIVE EXAMPLE 1

Ethylene glycol mono-n-hexyl ether.

COMPARATIVE EXAMPLE 2

Diethylene glycol mono-n-hexyl ether.

COMPARATIVE EXAMPLE 3

Propylene glycol mono-n-butyl ether.

COMPARATIVE EXAMPLE 4

Propylene glycol methyl ether acetate.

COMPARATIVE EXAMPLE 5

Propylene glycol di-n-butyl ether.

COMPARATIVE EXAMPLE 6

Limonene

COMPARATIVE EXAMPLE 7

Diethylene glycol monobutyl ether.

COMPARATIVE EXAMPLE 8

Diethylene glycol diethyl ether.

As is apparent from the data shown Table 1, in Comparative Example 2, the detergency is poor although the separability from water is good. In Comparative Example 6 (limonene, which is a terpene), the flash point is low, thus rendering safety poor, although the separability from water and detergency are good. In Comparative Example 7, the separability from water is poor, although the detergency is good. In Comparative Example 8, the separability from water is poor, although the detergency is good.

TABLE 1

| | Compound | Boiling point (°C.) | Flash point (°C.) | Solubility (%)(20° C.) | | Separability from water | Detergency | |
| | | | | (Water in) | (In water) | | Degreasing rate | Rosin dissolution rate |
| --- | --- | --- | --- | --- | --- | --- | --- | --- |
| Example 1 | Propylene glycol methyl cyclohexyl ether (PGMCHE) | 175 | 73 | 1.4 | 0.3 | Separated well | 99% or more | 30% or more |
| Example 2 | Propylene glycol ethyl cyclohexyl ether (PGECHE) | 192 | 80 | 0.7 | 0.2 | Separated well | 99% or more | 30% or more |
| Example 3 | Propylene glycol methyl 2-hydroxy-cyclohexyl ether (PGMHCHE) | 93* | 124 | 11.7 | 2.7 | — | — | — |
| Comparative Example 1 | Ethylene glycol mono-n-hexyl ether | 208 | 82 | 18.8 | 1.0 | — | — | — |
| Comparative | Diethyleneglycol | 259 | 140 | 56.3 | 1.7 | Separated | Less than | Less than |

TABLE 1-continued

| | Compound | Boiling point (°C.) | Flash point (°C.) | Solubility (%)(20° C.) (Water in) | (In water) | Separability from water | Detergency Degreasing rate | Rosin dissolution rate |
|---|---|---|---|---|---|---|---|---|
| Example 2 | mono-n-hexyl ether | | | | | well | 90% | 15% |
| Comparative Example 3 | Propylene 1 mono-n-butyl ether | 170 | 59 | 14.9 | 5.6 | — | — | — |
| Comparative Example 4 | Propylene glycol monomethyl ether acetate | 146 | 47 | 19.0 | 3.0 | — | — | — |
| Comparative Example 5 | Propylene glycol di-n-butyl ether | 190 | 69 | 0.6 | 2.0 | — | — | — |
| Comparative Example 6 | Limonene | — | 45 | — | — | Separated Well | 99% or more | 30% or more |
| Comparative Example 7 | Diethylene glycol monobutyl ether | — | 116 | — | — | Not separated | 99% or more | 30% or more |
| Comparative Example 8 | Diethylene glycol diethyl ether | — | 72 | — | — | Not separated | 99% or more | 30% or more |

[Note]*: Measured at 5 mm/Hg.

COMPARATIVE EXAMPLE 9

19 g (0.3 mole) of propylene oxide and 50 g (0.5 mole) of cyclohexanol were reacted in the presence of 1 g (0.025 mole) of sodium hydroxide at 150° C. for 1 hour, to thereby obtain 30 g of 1-cyclohexyloxy-2-propanol, i.e., propylene glycol cyclohexyl ether (PGCHE) (which is disclosed in Unexamined Japanese Patent Application Laid-Open Specification Nos. 4-57897 and 4-57898).

Properties of the product were measured and results of the measurements are shown in Table 2, together with those of Example 1 for easy comparison.

As apparent from Table 2, the results of Example 1 are very superior to the results of Comparative Example 9, particularly in relative drying rate, low viscosity, low solubility in water and oil solubility characteristics.

210, manufactured by Toho Chemical Industries Co., Ltd., Japan) and 5% by weight of triethenolamine were mixed, to thereby formulate a detergent composition. Then, the obtained detergent composition was subjected to testing of flux detergency in accordance with the following method.

A flux (F-230V, manufactured by Tamura Seisakusho Co., Ltd., Japan) was coated on a printed circuit board made of glass/epoxy resin and the coated board was dipped in a molten solder bath to thereby conduct soldering. Then, the obtained soldered board was immersed in the above-obtained detergent composition for 2 minutes while ultrasonically cleaning, and then rinsed with water. The evaluation of detergency was made by judging the amount of the flux remaining on the board by the naked eye. Results are shown in Table 3.

EXAMPLES 5 TO 7

TABLE 2

| | Example 1 | Comparative Example 9 |
|---|---|---|
| Compound | Propylene glycol methyl cyclohexyl ether (PGMCHE) | 1-cyclohexyloxy-2-propanol (PGCHE) |
| Structure | cyclohexyl—O—CH(CH$_3$)—CH$_2$—O—CH$_3$ | H—O—CH(CH$_3$)—CH$_2$—O—cyclohexyl |
| Boiling point (°C.) | 175 | 208 |
| Flash point (°C.) | 73 | 88 |
| Relative drying rate (%) | 77 | 36 |
| Viscosity (cP) | 2.4 | 14 |
| Solubility (%) (in water) | 0.3 | 1 |
| Oil solubility characteristics | | |
| (Mineral oil) | A | A |
| (Drawing oil) | A | E |
| (Press oil) | A | A |
| (Rosin oil) | A | C |

EXAMPLE 4

60% by weight of PGMCHE obtained in Example 1, 30% by weight of petroleum solvent (No. 0 Solvent M, manufactured by Nippon Sekiyu Kagaku Co., Ltd., Japan), 5% by weight of a polyoxyethylene nonyl phenyl ether-type nonionic surface active agent (Nonal Substantially the same procedure as in Example 4 was repeated except that the formulation of the detergent composition was changed as shown in Table 3. Results are also shown in Table 3.

TABLE 3

|  | Example 4 | Example 5 | Example 6 | Example 7 |
|---|---|---|---|---|
| Formulation of detergent (% by weight) |  |  |  |  |
| PGMCHE | 60 | 90 | — | — |
| PGECHE | — | — | 90 | 50 |
| Petroleum solvent | 30 | — | — | 30 |
| Triethanolamine | 5 | — | — | 10 |
| Nonionic surface active agent | 5 | 10 | 10 | 10 |
| Flux detergency | good | good | good | good |

Note
PGMCHE: Propylene glycol methyl cyclohexyl ether
PGECHE: Propylene glycol ethyl cyclohexyl ether
Petroleum solvent: No. 0 Solvent M ®
Nonionic surface active agent: Nonal 210 ®
The evaluation "good" means that substantially no flux remained.

EXAMPLE 8

508.3 g of a polyol having a molecular weight of 843 was charged in a four-necked flask provided with a thermometer, a stirrer and a reflux condenser and subjected to dehydration at 100° C. under reduced pressure (5 mmHg or less), and then allowed to cool to 60° C. Into the flask, 303.7 g of methyl ethyl ketone (hereinafter referred to as "MEK") was further added and allowed to cool to room temperature. Then, to the resultant mixture, 62.5 g of dimethylolpropionic acid (hereinafter referred to as "DMPA"), 47.2 g of triethylamine (hereinafter referred to as "TEA"), 29.4 g of trimethylolpropane (hereinafter referred to as "TMP"), 518.9 g of hydrogenated MDI were added, and then 847.2 g of MEK was further added. The resultant mixture was refluxed for 10 hours at 80° C. to obtain a solution of a prepolymer having a terminal isocyanate group. The obtained solution was allowed to cool to 25° C., and 2359 g of water was dropwise added over a period of 10 minutes to emulsify the solution. To the emulsion, a solution obtained by dissolving 49.4 g of isophoronediamine (hereinafter referred to as "IPDA") in 362 g of water, was dropwise added to effect a chain extension. Then, 116.6 g (10% by weight, based on the weight of the dispersed solid phase) of PGMCHE obtained in Example 1 was added. Neither a customary anti-foaming agent nor a customary film-forming agent was used. The temperature of the resultant mixture was elevated while passing a nitrogen gas through the flask to remove MEK, to thereby obtain an aqueous polyurethane dispersion composition (polyurethane emulsion). In the removal of MEK, foaming was slight.

The thus obtained composition (nonvolatiles content: 30% or more) was coated on a glass plate by means of a wire bar to form a 30 μm-thick film on the plate. The thus obtained film was uniform and neither cissing nor pinhole was observed therein. Further, the drying time was advantageously short.

EXAMPLE 9

An aqueous polyurethane dispersion composition was obtained in substantially the same manner as in Example 8 except that 349.8 g (25% by weight, based on the weight of the dispersed solid phase) of the PGMCHE obtained in Example 1 was used. Thereafter, the obtained composition was coated on a glass plate in the same manner as in Example 8. The thus obtained film was uniform and neither cissing nor pinhole was observed therein, and the drying time was advantageously short.

EXAMPLES 10 TO 15

An aqueous polyurethane dispersion composition was obtained in substantially the same manner as in Example 8 except that the formulation was changed as indicated in Table 4. Propylene glycol t-butyl cyclohexyl ether (PGtBCHE) used in Example 10 was synthesized in the same manner as in Example 1 except that 40 g (0.3 mole) of propylene glycol t-butyl ether was used in place of the propylene glycol methyl ether (PM) and the reaction temperature was changed to 80° C. Dipropylene glycol methyl cyclohexyl ether (DPGMCHE) used in Example 11 was synthesized in the same manner as in Example 1 except that 44 g (0.3 mole) of dipropylene glycol methyl ether was used in place of the PM. Propylene glycol isopropyl cyclohexyl ether (PGiPCHE) used in Example 12 was synthesized in the same manner as in Example 1 except that 35 g (0.3 mole) of propylene glycol isopropyl ether was used in place of the PM.

Results are shown in Table 4.

TABLE 4

|  | Example 10 | Example 11 | Example 12 | Example 13 | Example 14 | Example 15 |
|---|---|---|---|---|---|---|
| Formulation (g) |  |  |  |  |  |  |
| Hydrogenated MDI | 518.9 | 518.9 | 518.9 | — | — | — |
| IPDI | — | — | — | 439.8 | — | — |
| MDI | — | — | — | — | 495.0 | — |
| HDI | — | — | — | — | — | 332.8 |
| Polyol | 508.3 | 508.3 | 508.3 | 508.3 | 508.3 | 508.3 |
| TMP | 29.4 | 29.4 | 29.4 | 29.4 | 29.4 | 29.4 |
| DMPA | 62.5 | 62.5 | 62.5 | 62.5 | 62.5 | 62.5 |
| TEA | 47.2 | 47.2 | 47.2 | 47.2 | 47.2 | 47.2 |
| MEK | 1050.9 | 1050.9 | 1050.9 | 979.6 | 1029.4 | 883.2 |
| PGMCHE | — | — | — | 108.7 | 114.2 | 98.0 |
| PGtBCHE | 116.6 | — | — | — | — | — |
| DPGMCHE | — | 116.6 | — | — | — | — |
| PGiPCHE | — | — | 116.6 | — | — | — |
| Emulsifier | — | — | — | 5.4 | 5.7 | 4.9 |
| Foaming at the time of desolvation | Slightly foamed | Slightly foamed | Slightly foamed | Slightly foamed | Slightly foamed | Slightly foamed |
| Time needed for desolvation | 120 min | 120 min | 120 min | 120 min | 120 min | 120 min |
| Drying time at room temperature | 120 min | 120 min | 120 min | 120 min | 120 min | 120 min |

TABLE 4-continued

|  | Example 10 | Example 11 | Example 12 | Example 13 | Example 14 | Example 15 |
|---|---|---|---|---|---|---|
| Pinhole or cissing | none | none | none | none | none | none |

Note
MDI: Diphenylmethane-4,4-diisocyanate
IPDI: Isophorone diisocyanate
HDI: Hexamethylene diisocyanate
TMP: Trimethylolpropane
DMPA: Dimethylolpropionic acid
TEA: Triethylamine
MEK: Methyl ethyl ketone
PGMCHE: Propylene glycol methyl cyclohexyl ether
PGtBCHE: Propylene glycol t-butyl cyclohexyl ether
DPGMCHE: Dipropylene glycol methyl cyclohexyl ether
PGiPCHE: Propylene glycol isopropyl cyclohexyl ether
Emulsifier: Sodium polyoxyethylene alkyl phenyl ether sulfate (Levenol WZ ®, manufactured by Kao Co., Ltd., Japan)
The term "desolvation" means removal of MEK

EXAMPLE 16

Substantially the same procedure as in Example 8 was repeated except that 116.6 g (10% by weight, based on the weight of the dispersed solid phase) of PGMCHE was added during the production of the prepolymer. The obtained aqueous polyurethane dispersion composition was coated on a glass plate in the same manner as in Example 8. The thus obtained film was uniform and neither cissing nor pinhole was observed therein, and the drying time was advantageously short.

EXAMPLE 17

Substantially the same prepolymer synthesis as in Example 16 was repeated except that MEK was not used but the amount of PGMCHE was increased to 1267.5 g. The obtained prepolymer was subjected to emulsification and then to chain extension. Then, under reduced pressure, the PGMCHE content was reduced to about 10% by weight, based on the weight of the dispersed solid phase. The obtained aqueous polyurethane dispersion composition was coated on a glass plate in the same manner as in Example 16. The thus obtained film was uniform and neither cissing nor pinhole was observed, and the drying time was advantageously short.

COMPARATIVE EXAMPLE 10

An aqueous polyurethane dispersion composition was obtained in substantially the same manner as in Example 8 except that 40% by weight, based on the weight of the dispersed solid phase, of PGMCHE was used. The obtained composition was coated on a glass plate in the same manner as in Example 8, to thereby form a film on the plate. With respect to the thus obtained film, the drying time was disadvantageously, largely prolonged. Results are shown in Table 5.

COMPARATIVE EXAMPLE 11

Substantially the same procedure as in Example 8 was repeated except that PGMCHE was not used. However, a drastic foaming occurred at the time of desolvation, so that it was difficult to conduct desolvation. Results are shown in Table 5.

COMPARATIVE EXAMPLE 12

An aqueous polyurethane dispersion composition was obtained in substantially the same manner as in Example 8 except that PGMCHE was not used and that desolvation was conducted after adding 0.5% by weight of a mineral oil-type anti-foaming agent (Microwax, manufactured by Asahi Kasei Kogyo K.K., Japan) and 10% by weight of N-methylpyrrolidone, based on the weight of the dispersed solid phase. The obtained composition was coated on a glass plate in the same manner as in Example 8. As a result, over the entire surface of the obtained film, formation of pinholes occurred, and thus this film was not able to be practically used. Results are shown in Table 5.

COMPARATIVE EXAMPLE 13

Substantially the same procedure as in Comparative Example 12 was repeated except that a mineral oil-type anti-forming agent was not used. As a result, a drastic foaming occurred at the time of desolvation, so that it was difficult to conduct desolvation. Results are shown in Table 5.

COMPARATIVE EXAMPLE 14

An aqueous polyurethane dispersion composition was obtained in substantially the same manner as in Example 8 except that PGMCHE was not used and that 40% by weight, based on the weight of the dispersed solid phase, of hexyl cellosolve was used. The obtained composition was coated on a glass plate in the same manner as in Example 8. The drying time, however, was disadvantageously, largely prolonged. Results are shown in Table 5.

TABLE 5

|  | Comparative example 10 | Comparative example 11 | Comparative example 12 | Comparative example 13 | Comparative example 14 |
|---|---|---|---|---|---|
| Formulation of detergent (g) | | | | | |
| Hydrogenated MDI | 518.9 | 518.9 | 518.9 | 518.9 | 518.9 |
| Polyol | 508.3 | 508.3 | 508.3 | 508.3 | 508.3 |
| TMP | 29.4 | 29.4 | 29.4 | 29.4 | 29.4 |
| DMPA | 62.5 | 62.5 | 62.5 | 62.5 | 62.5 |
| TEA | 47.2 | 47.2 | 47.2 | 47.2 | 47.2 |
| MEK | 1050.9 | 630.5 | 1050.9 | — | 630.5 |
| PGMCHE | 466.5 | — | — | — | — |
| Hexyl cellosolve | — | — | — | — | 116.6 |

TABLE 5-continued

| | Comparative example 10 | Comparative example 11 | Comparative example 12 | Comparative example 13 | Comparative example 14 |
|---|---|---|---|---|---|
| N-methyl-pyrrolidone | — | — | 116.6 | 116.6 | — |
| Anti-foaming agent | — | — | 5.8 | — | — |
| Emulsifier | 5.8 | 5.8 | 5.8 | 5.8 | 5.8 |
| Foaming at the time of desolvation | Slightly foamed | Drastically foamed | Slightly foamed | Drastically foamed | Moderately foamed |
| Time need for desolvation | 120 min | 240 min | 120 min | 240 min | 240 min |
| Drying time at room temperature | 360 min | 120 min | 120 min | 120 min | 240 min |
| Pinhole or cissing | none | none | Pinholes formed | none | none |

Note
TMP: Trimethylolpropane
DMPA: Dimethylolpropionic acid
TEA: Triethylamine
MEK: Methyl ethyl ketone
PGMCHE: Propylene glycol methyl cyclohexyl ether
Emulsifier: Sodium polyoxyethlene alkyl phenyl ether sulfate (Levenol WZ ®, manufactured by Kao, Co., Ltd., Japan)

EXAMPLE 18

To 100 g of an aqueous polyacrylate dispersion (polyacrylate emulsion) (Polytron E-400, manufactured by Asahi Kasei Kogyo K.K., Japan; solids content: 50% by weight), 5 g (10% by weight based on the weight of the dispersed solid phase) of PGMCHE was added while stirring at room temperature, to thereby obtain an aqueous polyacrylate dispersion composition. With respect to the obtained composition, the viscosity was measured. Further, the minimum film-forming temperature of the composition was measured using a minimum film-forming temperature measuring apparatus manufactured by Takabayashi Rika Co., Ltd, Japan. Then, the composition was tested with respect to the film forming properties at a low temperature and the drying rate in accordance with the following methods.

(1) Film Forming Properties at a Low Temperature

The aqueous dispersion composition was coated on a glass plate to form a 250 μm-thick film which was in a wet state. The film was immediately placed in a drying machine kept at 3° C. to dry the film. Then, the appearance of the film was evaluated as follows.

○: Uniform film with no defects was formed.
Δ: A part of the surface was cracked.
X: Entire surface was cracked.

(2) Drying Rate

The aqueous dispersion composition was coated on a glass plate to form a 250 μm-thick film which was in a wet state and, was immediately allowed to stand still in a constant-temperature chamber at 20° C. and at a relative humidity of 65%. The drying time was evaluated by dropping 0.1 ml of water on the film surface, after periods of 30 minutes, 1 hour, 2 hours, 4 hours, 8 hours, 1 day, 2 days, 4 days and 8 days from the time of the coating. When the film did not become white turbid after 5 minutes from the dropping of water, the period of time between the start of the drying and the dropping of water was taken as the drying time. Results are shown in Table 6.

EXAMPLES 19 TO 24

An aqueous polyacrylate dispersion composition was obtained in substantially the same manner as in Example 18 except that the type and amount of the propylene glycol cyclohexyl ether derivative and the type of the aqueous polyacrylate dispersion were changed as shown in Table 6. [In Examples 22 to 24, a poly(acrylatestyrene) emulsion (Polytron F-2200, manufactured by Asahi Kasei Kogyo K.K., Japan) was used.] The obtained composition was coated on a glass plate in the same manner as in Example 18. With respect to the resultant film, the viscosity, minimum film-forming temperature, film-forming properties at a low temperature, and drying time were measured, and results are shown in Table 6.

COMPARATIVE EXAMPLE 15

To 100 g of an aqueous polyacrylate dispersion (Polytron E-400, manufactured by Asahi Kasei Kogyo K.K., Japan; solids content: 50% by weight), 5 g (10% by weight based on the weight of the dispersed solid phase) of 2,2,4-trimethyl-1,3-pentanediol isobutyrate (CS-12, manufactured by Chisso Co., Ltd., Japan) as a film-forming agent was added while stirring at room temperature, to thereby obtain an aqueous polyacrylate dispersion composition. The obtained composition was coated on a glass plate in the same manner as in Example 18. With respect to the resultant film, the viscosity, minimum film-forming temperature, film-forming properties at a low temperature, and drying time were measured, and results are shown in Table 6.

COMPARATIVE EXAMPLE 16

Substantially the same procedure as in Comparative Example 15 was repeated except that 12.5 g (25% by weight based on the weight of the dispersed solid phase) of 2,2,4-trimethyl-1,3-pentanediol isobutyrate (CS-12) was used. The properties of the resultant film were measured in the same manner as in Comparative Example 15, and results are shown in Table 6.

COMPARATIVE EXAMPLES 17 AND 18

Substantially the same procedure as in Comparative Example 15 was repeated except that in Comparative Examples 17 and 18, butyl cellosolve and polypropylene glycol (Ratemuru-1040, manufactured by Kao Co., Ltd., Japan) were, respectively, used as a film-forming agent. The properties of the resultant film were measured in the same manner as in Comparative Example 15 and results are shown in Table 6.

TABLE 6

| | Example 18 | Example 19 | Example 20 | Example 21 | Example 22 | Example 23 | Example 24 | Comparative example 15 | Comparative example 16 | Comparative example 17 | Comparative example 18 |
|---|---|---|---|---|---|---|---|---|---|---|---|
| Aqueous emulsion | Polyacrylate emulsion (100 g) | | | | Poly(acrylate-styrene) emulsion (100 g) | | | Polyacrylate emulsion (100 g) | | | |
| Amount of film forming agent (g): | | | | | | | | | | | |
| PGMCHE | 5 | 0.5 | 12.5 | | 5 | 12.5 | | | | | |
| DPGMCHE | | | | 5 | | | 5 | | | | |
| Isobutyrate | | | | | | | | 5 | 12.5 | | |
| Butyl cellosolve | | | | | | | | | | 5 | |
| Polypropylene glycol | | | | | | | | | | | 5 |
| Viscosity (cps) | 410 | 350 | 3800 | 440 | 400 | 3500 | 400 | 510 | 6200 | 550 | 650 |
| Minimum film forming temperature (°C.) | 18 | 35 | 4 | 19 | 28 | 14 | 30 | 29 | 14 | 27 | 32 |
| Film forming properties at low temperature | ○ | ○ | ○ | ○ | ○ | ○ | ○ | △ | △ | △ | x |
| Drying time | 2 hours | 1 hour | 4 hours | 2 hours | 2 hours | 4 hours | 2 hours | 4 hours | 8 hours | 4 hours | 8 days |

Note
PGMCHE: Propyrene glycol methyl cyclohexyl ether
DPGMCHE: Dipropyrene glycol methyl cyclohexyl ether
Isobutyrate: CS-12 ® (2,2,4-trimethyl-1,3-pentanediol isobutyrate)
Polypropylene glycol: Ratemuru ®
Polyacrylate emulsion: Polytron ® E-400
Poly(acrylate-styrene) emulsion: Polytron ® F-2200
○: Uniform film was formed
△: A part of surface was cracked
x: Entire surface was cracked

What is claimed is:

1. A propylene glycol cyclohexyl ether derivative represented by the formula (I)

$$\text{cyclohexyl}(R^2)\text{--}(\text{OCHCH}_2)_n\text{OR}^1 \quad \text{with CH}_3 \text{ substituent} \tag{I}$$

wherein $R^1$ represents a straight or branched alkyl group having 1 to 6 carbon atoms, or a cycloalkyl group having 3 to 6 carbon atoms; $R^2$ represents a hydrogen atom or a hydroxyl group; and n represents an integer of from 1 to 3.

2. The propylene glycol cyclohexyl ether derivative according to claim 1, which is propylene glycol methyl cyclohexyl ether, propylene glycol methyl monohydroxycyclohexyl ether or dipropylene glycol methyl cyclohexyl ether.

3. A method for producing a propylene glycol cyclohexyl ether derivative represented by the formula (I)

$$\text{cyclohexyl}(R^2)\text{--}(\text{OCHCH}_2)_n\text{OR}^1 \quad \text{with CH}_3 \text{ substituent} \tag{I}$$

wherein $R^1$ represents a straight or branched alkyl group having 1 to 6 carbon atoms, or a cycloalkyl group having 3 to 6 carbon atoms; $R^2$ represents a hydrogen atom or a hydroxyl group; and n represents an integer of from 1 to 3, which comprises reacting a propylene glycol ether represented by the formula (II)

$$\text{H--(OCHCH}_2)_n\text{OR}^1 \quad \text{with CH}_3 \text{ substituent} \tag{II}$$

wherein $R^1$ represents a straight or branched alkyl group having 1 to 6 carbon atoms, or a cycloalkyl group having 3 to 6 carbon atoms; and n represents an integer of from 1 to 3, with cyclohexene, cyclohexanol or cyclohexene oxide in the presence of a catalyst.

4. A detergent comprising at least one propylene glycol cyclohexyl ether derivative represented by the formula (I)

$$\text{cyclohexyl}(R^2)\text{--}(\text{OCHCH}_2)_n\text{OR}^1 \quad \text{with CH}_3 \text{ substituent} \tag{I}$$

wherein $R^1$ represents a straight or branched alkyl group having 1 to 6 carbon atoms, or a cycloalkyl group having 3 to 6 carbon atoms; $R^2$ represents a hydrogen atom or a hydroxyl group; and n represents an integer of from 1 to 3.

5. The detergent according to claim 4, wherein said at least one propylene glycol cyclohexyl ether derivative is selected from the group consisting of propylene glycol methyl cyclohexyl ether, propylene glycol methyl monohydroxycyclohexyl ether and dipropylene glycol methyl cyclohexyl ether.

6. An aqueous dispersion composition comprising:

(a) a continuous phase of an aqueous dispersion medium;

(b) a dispersed phase dispersed in said continuous phase (a); and (c) 0.5–30% by weight, based on the weight of said dispersed phase (b), of at least one propylene glycol cyclohexyl ether derivative represented by the formula (I):

$$\text{(I)} \quad \underset{R^2}{\underset{|}{\bigcirc}}\!\!-\!(\text{OCHCH}_2)_{\overline{n}}\text{OR}^1 \quad \overset{CH_3}{\underset{|}{}}$$

wherein $R^1$ represents a straight or branched alkyl group having 1 to 6 carbon atoms, or a cycloalkyl group having 3 to 6 carbon atoms; $R^2$ represents a hydrogen atom or a hydroxyl group; and n represents an integer of from 1 to 3.

7. The composition according to claim 6, wherein said dispersed phase consists essentially of a polyurethane or a polyacrylate.

8. The composition according to claim 6, wherein said at least one propylene glycol cyclohexyl ether derivative is selected from the group consisting of propylene glycol methyl cyclohexyl ether, propylene glycol methyl monohydroxycyclohexyl ether or dipropylene glycol methyl cyclohexyl ether.

* * * * *